Oct. 16, 1934. G. DE RUYTER Plant Pat. 106
VARIETY OF ROSE
Filed Feb. 3, 1934
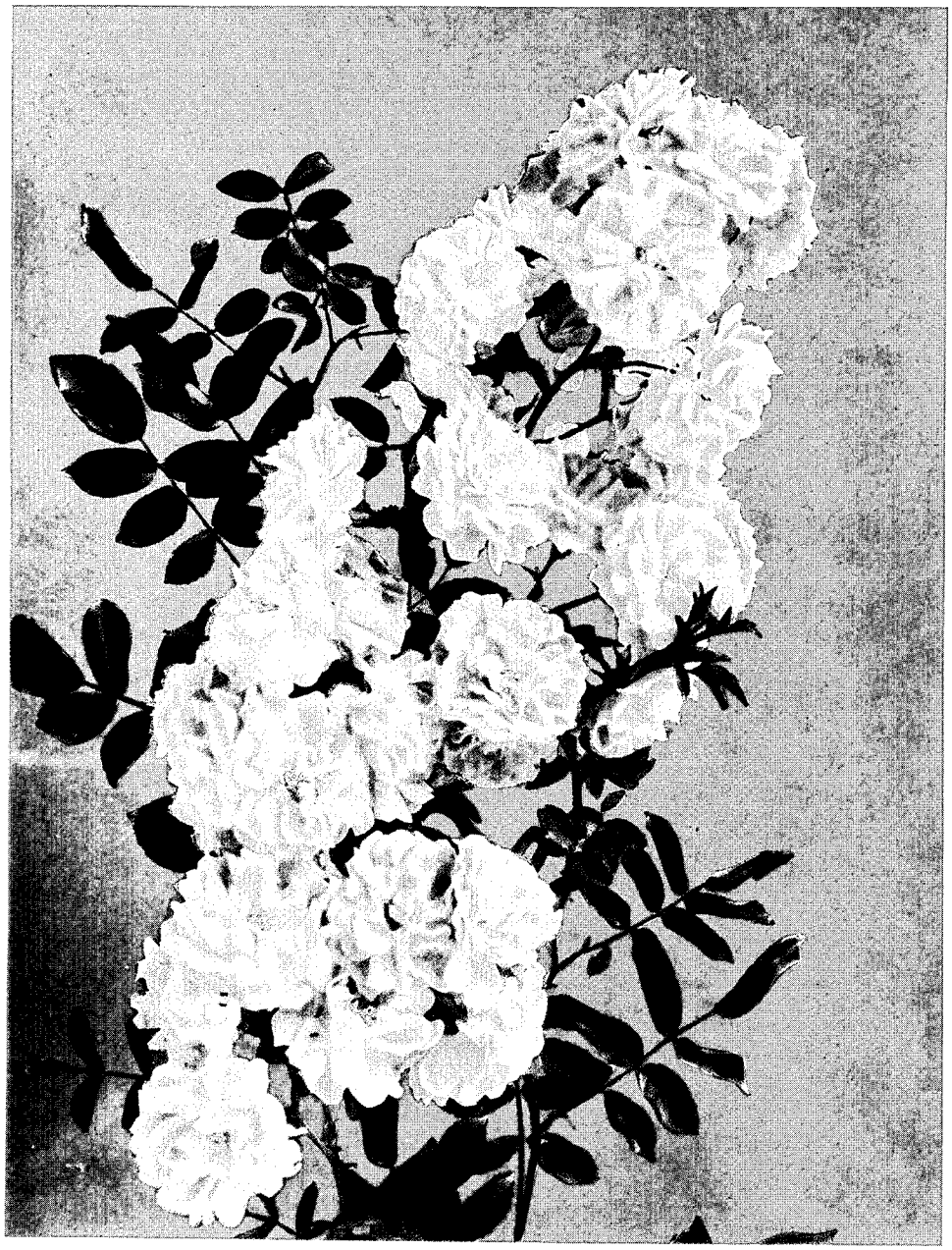
Inventor
Gerrit de Ruyter
By Robb & Robb
Attorneys

UNITED STATES PATENT OFFICE

106

VARIETY OF ROSE

Gerrit de Ruyter, Hazerswonde, Netherlands, assignor to Jackson & Perkins Company, Newark, N. Y.

Application February 3, 1934, Serial No. 709,667

1 Claim. (Cl. 47—61)

The present invention or discovery relates to a new variety of rose and may be described as a climbing sport of the dwarf Polyantha rose "Gloria Mundi". As such it is unique and novel because, so far as I am aware, no climbing rose exists with the same brilliant orange scarlet color that distinguishes Gloria Mundi among the dwarf Polyanthas.

This new rose is a rampant climber and as such is particularly suited for covering trellisses, pergolas, and other tall supports. It is also adapted to florist uses such as basket work and any type of floral decoration for which climbers and ramblers are now used.

This new rose has been asexually propagated and found to produce true to form.

For a more detailed description of this new rose the following tabulated description is noted:—

Parentage—
Sport of Gloria Mundi.

Classification—
Climbing Rosa Polyantha.

*Flower*

Blooming habit—
Blooms in midseason, profusely; has a tendency to give few blooms in the fall.

Bud—
*Size.*—Small.
*Form.*—Short, globular; unaffected by wet or hot weather.
*Color.*—Orange scarlet.
*Sepals.*—Smooth edge; curl back as each bloom opens.
*Calyx.*—Apple shape; broad, hairy, and without odor when rubbed.
*Peduncle.*—Length—medium; aspect—hairy; color—light green; strength—stiff; erect.
*Opening.*—Opens well; unaffected by adverse conditions.

Bloom—
*Size.*—Small; average size when fully expanded three to three and one-half centimeters.
*Borne.*—Several together, in clusters; pyramidal.
*Stems.*—Long; strong.
*Form.*—When first open it is cupped; retains its form to the end; all petals curl quill fashion.
*Petalage.*—Very double (many petals and stamens hidden), the number of petals under normal conditions being thirty-five to forty.
*Color.*—Center of flower orange scarlet, outer petals orange scarlet, base of petals whitish, inside of petals orange scarlet, reverse of petals orange scarlet.

Petals—
*Texture.*—Thin, soft; affected by wet or hot weather—edges might sunburn a little.
*Appearance.*—Inside shiny, velvety; outside satiny.
*Form.*—Round, oval, scalloped.
*Arrangement.*—Many small petaloids in center.
*Persistence.*—Drop off cleanly.
*Fragrance.*—None.
*Lastingness.*—On the plant and as a cut flower very long.

Genital organs—
*Stamens, anthers.*—Small, many. Color—white. Arrangement—regular around styles, mixed with petaloids.
*Stamens, filaments (threads).*—Short. Color—yellow.
*Pollen.*—Gold yellow.
*Styles.*—Loosely separated, uneven length; short, thin.
*Stigmas.*—Greenish-yellow.

Fruit—
Variety is sterile with its own pollen.

*Plant*

Form—
Rambler.

Growth—
Vigorous.

Foliage—
*Size.*—Medium.
*Quantity.*—Normal.
*Color.*—New foliage—upper side, light green; under side, light green. Old foliage—upper and under side normal green.
*Shape.*—Oval pointed.
*Texture.*—Upper side glossy, corrugated. Under side, rough. Ribs and veins—Prominent, ordinary, light, impressed.
*Edge.*—Serrated (saw toothed).
*Serration.*—Single, small.
*Leaf stem.*—Color, reddish. Under side, rough prickles.
*Stipules.*—Long, serrated, bearded.
*Disease resistance.*—Susceptible to mildew.

Wood—
*New wood.*—Color, light green. Bark—smooth.
*Old wood.*—Color, green. Bark—smooth.

Thorns—
*Thorns.*—On laterals from stalk, ordinary. Form—flat base, medium, hooked downward. Color when young—green and red. Position—irregular, in pairs, in sets of three or more, two under each leaf, one in between.
*Prickles.*—Few, on main stalks and laterals. Color—brown.
*Short needles.*—None on laterals.

It will be understood that the Gloria Mundi from which the present variety sported is known as a Baby Rose or Dwarf Polyantha as hereinbefore indicated and that it seldom grows to a height of over fifteen inches. On the other hand this new variety above described is a rampant climbing form of said Gloria Mundi and reproductions of the same show that canes run up twelve to fifteen feet in a single season. It is this climbing feature in combination with the color of the bloom which marks the point of distinction of this variety from the prior known varieties of rose plants.

I claim:—

A new and distinct variety of rose plant characterized by its rampart climbing habit, as described, and the orange-scarlet color of its bloom, as shown.

GERRIT DE RUYTER.